(12) United States Patent
De Jong et al.

(10) Patent No.: US 7,446,074 B2
(45) Date of Patent: Nov. 4, 2008

(54) HIGHLY CONCENTRATED, STABLE, AND SAFE DIACYL PEROXIDE AND PEROXYDICARBONATE EMULSIONS WITH A LOW CHEMICAL OXYGEN DEMAND VALUE

(75) Inventors: Johannes Jacobus Theodorus De Jong, Westervoort (NL); Boen Ho O, Utrecht (NL); Hans Westmijze, Bathmen (NL)

(73) Assignee: Akzo Nobel N.V., Arnhem (NL)

( * ) Notice: Subject to any disclaimer, the term of this patent is extended or adjusted under 35 U.S.C. 154(b) by 309 days.

(21) Appl. No.: 10/512,762

(22) PCT Filed: Apr. 24, 2003

(86) PCT No.: PCT/EP03/04363

§ 371 (c)(1),
(2), (4) Date: Dec. 23, 2004

(87) PCT Pub. No.: WO03/095500

PCT Pub. Date: Nov. 20, 2003

(65) Prior Publication Data

US 2005/0171275 A1 Aug. 4, 2005

(30) Foreign Application Priority Data

May 8, 2002 (EP) .................................. 02076801

(51) Int. Cl.
*C08F 4/28* (2006.01)
(52) U.S. Cl. ....................... 502/160; 524/562; 526/227; 526/228; 526/230; 526/230.5; 526/344
(58) Field of Classification Search ................. 502/160; 524/562; 526/227, 228, 230, 230.5, 344
See application file for complete search history.

(56) References Cited

U.S. PATENT DOCUMENTS 3,988,261 A * 10/1976 Barter et al. ................. 502/160
4,499,250 A * 2/1985 Lundin et al. ................ 526/209
6,350,835 B1 * 2/2002 O et al. ........................ 526/202

FOREIGN PATENT DOCUMENTS

| EP | 0 032 757 A2 | | 7/1981 |
| EP | 0 998 456 B1 | | 3/2003 |
| JP | 11171914 A | * | 6/1999 |
| JP | A 2001-64321 | | 3/2001 |

OTHER PUBLICATIONS

Kenneth Mason Publications, Research Disclosure, Hampshire, GB, vol. 215, pp. 63, Mar. 1, 1982.
Akzo Nobel Chemicals B. V. brochure, "Imitiators for High Polymers," with code 10737, pp. 1-24.
Akzo Nobel Chemicals B. V. brochure, "Initiators for High Polymers," with code 1000225, pp. 1-20.
"The HLB System a time-saving guide to emulsifier selection," Atlas Chemical Industries, Inc., 1980.
Stache, et al., "Tensid-Taschenbuch," Carl Hanser Verlang Munchen Wein, pp. 68-71, 1979.
Tadros, "Applied Surfacants," Wiley-VCH Verlag Gmbh & Co. KgaA, pp. 134-137, 2005.
BASF The Chemical Company, "Tenside and Polyalkylenglykole," 2001.

* cited by examiner

*Primary Examiner*—Bernard Lipman
(74) *Attorney, Agent, or Firm*—Kenyon & Kenyon LLP

(57) ABSTRACT

The invention relates to highly concentrated aqueous emulsions of peroxides comprising an anti-freeze agent, a polyvinyl acetate with a degree of hydrolysis between 45 and 80%, and optionally a non-ionic surfactant with an HLB value greater than 10 selected from alkylene oxide block-copolymers, ethoxylated fatty alcohols, and ethoxyfated fatty acids. The emulsions have a low COD value and are safe, storage stable, and generally applicable.

16 Claims, No Drawings

HIGHLY CONCENTRATED, STABLE, AND SAFE DIACYL PEROXIDE AND PEROXYDICARBONATE EMULSIONS WITH A LOW CHEMICAL OXYGEN DEMAND VALUE

The invention relates to aqueous emulsions of diacyl and/or peroxydicarbonate peroxides comprising a protective colloid, a non-ionic emulsifier, and an anti-freeze agent.

Such peroxide emulsions are known from British patent GB 2 068 008, which discloses emulsions comprising a peroxydicarbonate, a non-ionic emulsifier, and a protective colloid. The non-ionic emulsifier can be chosen from a wide variety of compounds including an ethoxylated fatty alcohol and most preferably an ethoxylated fatty acid. Similarly, the protective colloid can be selected from a myriad of components. The peroxydicarbonate emulsions disclosed in GB 2 068 008 have relatively low peroxide concentrations of up to 30% by weight (% w/w). It is known in the art that if the peroxide concentration is increased, an increase in the volume average peroxide droplet size (d50) and an increase in the 99 percentile droplet size distribution (d99) will result or, even worse, separation of the peroxide from the aqueous emulsion. In any case, the values for d50 and d99 will increase over time, eventually rendering the emulsion unstable and unsafe. Also the viscosity is known to increase to an unacceptable level if the peroxide concentration in conventional formulations is increased.

The stability and safety of emulsions with 40% w/w peroxydicarbonate is improved when propylene glycol is added as anti-freeze agent in an amount of 25% by weight, as is described in JP2001064321. The chemical oxygen demand (COD) value of in particular the aqueous phase of these emulsions, however, is unacceptably high, which is highly undesirable particularly from an environmental point of view.

It is an object of the present invention to provide an aqueous emulsion of a diacyl peroxide and/or a peroxydicarbonate with a high peroxide concentration which has an improved COD value of the aqueous phase, particularly in relation to the amount of peroxide in the organic phase, which emulsion also has acceptable stability, viscosity, and safety characteristics.

We have now found that, surprisingly, improved aqueous peroxide emulsions can be produced and applied by a proper combination of diacyl peroxide and/or peroxydicarbonate, protective colloid, non-ionic surfactant, and anti-freeze agent. These emulsions not only have a low COD value, they also are more economical to produce and were found to be able to improve the properties of the polymer produced therewith.

The invention consists of a peroxide emulsion wherein the concentration of the peroxide ranges from 52.5 to 75% by weight and the protective colloid is a partly saponified polyvinyl acetate having a concentration of from 0.01 to 2.5% by weight, wherein the polyvinyl acetate has a degree of hydrolysis of at least 45 and at most 80%, and with a stabilizing amount of one or more non-ionic surfactants and/or one or more anti-freeze agents such that the result is a stable and safe formulation with an aqueous phase that has a low COD value. Despite the high concentration of the peroxide, such an emulsion has d50 and d99 values which do not substantially change over time, resulting in a very stable emulsion. Also, such emulsions were found to be storage safe and to have acceptable viscosity. Moreover, these emulsions generally have small peroxide droplet sizes, which is advantageous if they are used in polymerization reactions for which they are suitable. Such small droplet sizes and droplet size distributions enable better control of the process of polymerization, as the peroxide efficiency is enhanced, thereby improving the space-time yield of the said process. In the emulsion of the invention the amount of polyvinyl acetate (PVAc) can be very low, e.g., lower than 1%, which substantially decreases the cost of such an emulsion, as the PVA is expensive, and which reduces the COD value of the aqueous phase. Although the invention is suitable to produce emulsions of diacyl peroxides, peroxydicarbonate, and emulsions comprising a mixture of these two classes of peroxides, it is particularly suitable for preparing emulsions of peroxides that, when diluted to a concentration of 75% in isododecane, have a self-accelerating decomposition temperature (as determined according to conventional UN regulations) of 10° C. or less. Such peroxides or mixtures of peroxides typically require the use of anti-freeze agents when an emulsion is produced, resulting in emulsions with a high COD. More preferably, the emulsions according to the invention comprise at least one or more peroxydicarbonates, since here the reduction of the COD value, compared to conventional emulsions, is greatest. Most preferably, the emulsions of the present invention comprise essentially only one or more peroxydicarbonates.

The relatively low COD value of the aqueous phase of the emulsion ensures that the environmental burden is substantially reduced. The aqueous phase is defined as encompassing all constituents of the peroxide emulsion except for the peroxide itself and/or any organic diluent of the peroxide. The said COD value is defined as the mg of oxygen needed for oxidation of the organic compounds in 100 mg of the aqueous phase of the emulsion. The said COD value therefore depends on the amount of organic compounds, e.g., the anti-freeze agents and protective colloids, in the aqueous phase. The amount of anti-freeze added to the aqueous phase of the emulsion can be determined by the reduction in freezing point of the aqueous emulsion. It is commonly known that the freezing point decreases by about 18.6° C. per mole of anti-freeze dissolved in 100 g of water. In other words, emulsions may contain anti-freeze agents with a relatively low molecular weight in a smaller weight fraction than high-molecular weight agents to give the same freezing point decrease. The required freezing point decrease for a peroxide emulsion depends on the desired storage temperature, which is specific for each peroxide. For, example, for a di(2-ethylhexyl) peroxydicarbonate this storage temperature is −15° C., as is disclosed in the brochure entitled "Initiators for High Polymers" with code 1000225 from Akzo Nobel Chemicals B.V. If methanol and propylene glycol are compared, it is evident that fewer milligrams, of methanol than milligrams of propylene glycol are needed in the emulsion to obtain the same decrease in freezing point. Consequently, also taking into account that about 1.3 mg and about 1.7 mg of oxygen are needed for the oxidation of, respectively, 1 mg of methanol and 1 mg of propylene glycol, it is clear that the COD of the aqueous phase containing methanol is substantially lower than the COD of the aqueous phase containing propylene glycol with an equal freezing point. An acceptable COD value of the aqueous phase as far as an anti-freezing agent is concerned is at most 50 mg oxygen per 100 mg aqueous phase, preferably at most 40 mg oxygen per 100 mg aqueous phase, and most preferably at most 30 mg oxygen per 100 mg aqueous phase.

It is noted that the present invention relates to emulsions that are liquid when stored at the recommended storage temperature. Hence, it does not relate to products that are also know as "frozen emulsions," which are solids at the recommended storage temperature, and which typically contain very little or no anti-freeze.

The peroxide emulsions of the invention are concentrated, which is defined here as emulsions wherein the amount of peroxide exceeds 40% by weight. Preferably, the concentration of peroxide in the emulsions according to the invention is at least 52.5% w/w, more preferably at least 55% w/w, and most preferably at least 60% w/w. The peroxide concentration is at most 75% w/w, more preferably at most 70% w/w, and most preferably at most 65% w/w. These peroxide emulsions will ensure substantially reduced freight and handling costs in comparison with conventional peroxide emulsions containing 40% w/w or less of peroxide. The safety aspects of the final emulsion predominantly determine the high end of the peroxide concentration range. It was found that a proper selection of the water/anti-freeze content of the formulation will further enhance the safety characteristics. More specifically, when properly chosen, the water and the anti-freeze can dissipate the heat of decomposition of the peroxide.

The peroxide emulsions according to the invention preferably comprise a peroxide that is liquid or dissolved at −10° C., in particular a peroxide having a recommended storage temperature of 15° C. or less, more preferably a recommended storage temperature of 10° C. or less, even more preferably a recommended storage temperature of 0° C. or less, and most preferably a recommended storage temperature of −10° C. or less. Typically, the recommended storage temperature is specified by the producer of the peroxide. If the recommended storage temperature unknown, reference is made to the Akzo Nobel Chemicals B.V. brochure "Initiators for high polymers" with code 10737.

Peroxydicarbonates preferably used in the aqueous emulsions according to the invention include: di-sec-butyl peroxydicarbonate (TRIGONOX® SBP), dibutyl peroxdedicarbonate (TRIGONOX® NBP), diisopropyl peroxydicarbonate (TRIGONOX® IPP), di(2-ethylhexyl)peroxydicarbonate (TRIGONOX® EHP), (TRIGONOX® ADC), dibutyl peroxydicarbonate (TRIGONOX® NBP), bis(3-methoxybutyl) peroxy-dicarbonate, bis(isobutyl)peroxydicarbonate, dineopentyl peroxydicarbonate, bis(1-methylheptyl) peroxydicarbonate, bis[2-(2-methoxyethoxy)ethyl]peroxydicarbonate, bis(3-methoxy-3-methylbut-yl)peroxydicarbonate, and bis(2-ethoxyethyl)peroxydicarbonate. Other examples are dissolved distearyl peroxydicarbonate and dicyclohexyl peroxydicarbonate. Any appropriate inert phlegmatizing solvent can be used to dilute and/or dissolve any of the peroxydicarbonates. Such solvents are well known in the art and include for instance isododecane.

As said above, suitable diacyl peroxides for use in the aqueous emulsions according to the invention are those that are liquid or dissolved at −10° C. Preferred diacyl peroxides include: diisobutyroyl peroxide, di(3,5,5-trimethylhexanoyl) peroxide, di(2-ethylhexanoyl)peroxide, di(2-ethylbutanoyl) peroxide, and a-symmetrical diacyl peroxides, such as isobutyroyl octanoyl peroxide, isobutyroyl decanoyl per oxide, isobutyroyl lauroyl peroxide, 2-ethylbutanoyl decanoyl peroxide, and 2-ethylhexanoyl lauroyl peroxide. The most preferred diacyl peroxides comprise at least one isobutyroyl moiety of the formula

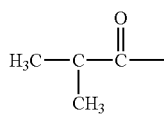

The protective colloid to be used in the aqueous emulsions according to the invention must be a PVAC with a degree of hydrolysis of at least 45, more preferably at least 48%, and most preferably at least 50%, and at most 80%, preferably at most 70%, more preferably at most 62.5%, and most preferably at most 60%. A PVAC with a degree of hydrolysis below 45% cannot be used because such a PVAC is not soluble in the mixture of water and anti-freeze. A PVAC with a degree of hydrolysis above 80% resulted in emulsions with a too high viscosity. Instead of using just one type of PVAC, also a blend of two or more PVACs can be used. In that case the blend can be seen as just one PVAC of which the degree of hydrolysis is the weight average degree of hydrolysis of the PVACs. Preferably, such a blend of PVACs does not comprise a PVAC with a degree of hydrolysis below 45% or above 80%, for the above-mentioned reasons. Celluloses were found not to be suitable, since the level at which they are to be used results in emulsions with a too high COD.

The amount of PVAC used in the emulsions according to the invention will depend on the concentration and the types of peroxides and surfactants used and the desired viscosity of the final emulsion. Typically, the amount of PVAC in the final emulsion will be at least 0.01% w/w, preferably at least 0.1% w/w, and most preferably 0.5% w/w, and at most 2.5% w/w, more preferably at most 2.0% w/w, even more preferably at most 1.5% w/w, and most preferably at most 1.0% w/w. The use of these protective colloids in combination with the above-mentioned surfactants enables the production of concentrated, storage-stable, and safe peroxydicarbonate emulsions. An acceptable COD value of the aqueous phase as far as PVAC is concerned is at most 5 mg oxygen per 100 mg aqueous phase, preferably at most 3 mg oxygen per 100 mg aqueous phase, more preferably at most 2 mg oxygen per 100 mg aqueous phase, and most preferably at most 1.5 mg oxygen per 100 mg aqueous phase.

Further, it is advantageous to add a non-ionic surfactant to the peroxide emulsion. In this specification, the term "surfactant" refers to the surface-active chemical that is to be used in the peroxide formulations according to the invention and that influences the interfacial surface tension between the water and the peroxide phase. Such compounds are also known as "emulsifiers." Preferably, the aqueous peroxide emulsion according to the invention contains only one surfactant with an HLB value of 15 or higher. More preferred are surfactants with an HLB value of at least 16, and most preferred are surfactants with an HLB value of at least 17. If so desired, a mixture of surfactants may be used. In that case, the combined surfactants should have an HLB value of 15 or higher, while it is preferred that all surfactants used have an HLB greater than 10, preferably greater than 12.5, and more preferably of 15 or higher, because surfactants with a lower HLB value can have an adverse effect on the viscosity of the final emulsion. As surfactants with an HLB of less than 10 undesirably increase the viscosity of the emulsion, sorbitan esters such as sorbitan oleate (HLB 4.3) and sorbitan laurate (HLB 8.5) are not suitable. HLB value stands for the hydrophilic-lipophilic balance, as described in "The Atlas HLB-System, a time saving guide to emulsifier selection," published by Atlas Chemical Industries Inc., 1963. For blends of surfactants the HLB value is calculated from the weight ratio of the components, as is also mentioned in this publication.

The non-ionic surfactant or surfactants that can be used in the aqueous emulsions according to the invention are alkylene oxide block-copolymers, ethoxylated fatty alcohols, and ethoxylated fatty acids. The preferred surfactants are ethoxylated fatty alcohols and ethoxylated fatty acids with an HLB value greater than 15. Most preferred are such ethoxylated fatty alcohols. Examples of suitable ethoxylated fatty alcohols include ethoxylated lauryl alcohol, e.g., with a degree of ethoxylation of 23, having an HLB-value of 16.9, and obtainable from ICI as BRIJ® 35, ethoxylated dodecyl alcohol, such as REMCOPAL® 20, ethoxylated myristyl alcohol, ethoxylated cetyl alcohol, ethoxylated oleyl alcohol, ethoxylated mixtures of alcohols, such as ETHYLAN® CO35, which is the ethoxylated product of a mixture of palmitic alcohol and oleyl alcohol, ethoxylated alcohols derived from coconut oil, palmitic acid, and/or tallow, and ethoxylated stearyl alcohol, e.g., with a degree of ethoxylation of 80 with an HLB-value of 18.5, and obtainable from Akzo Nobel as BEROL® 08. These products were found to be pre-eminently suited to make emulsions with good stability, safety, and viscosity properties at high peroxydicarbonate concentrations. Even with PVA concentrations below 1.0% w/w, the average droplet size of the peroxide is extremely small—generally smaller than 4 μm—with a relatively narrow droplet size distribution. Preferably, the amount of the surfactant or the combination of surfactants in the final emulsion is at least 0.01% w/w, preferably at least 0.02% w/w, and most preferably at least 0.05% w/w, and at most 5% w/w, preferably at most 2% w/w, and most preferably at most 1% w/w. An acceptable COD value of the aqueous phase as far as the surfactant is concerned is at most 20 mg. oxygen per 100 mg aqueous phase, preferably at most 10 mg oxygen per 100 mg aqueous phase, more preferably at most 5 mg oxygen per 100 mg aqueous phase, and most preferably at most 2 mg oxygen per 100 mg aqueous phase. Instead of the surfactant, or together with the surfactant, an anti-freeze is to be used in the emulsions according to the invention, so that the emulsion is pourable and/or pumpable at the recommended storage temperature and lower, which as can be gleaned from the brochure entitled "Initiators for High Polymers" with code 1000225 from Akzo Nobel Chemicals B.V., is specific for each peroxide-containing phase. The amount of freezing point suppressant to be used will depend on the type of anti-freeze, or mixture of anti-freeze agents, used. Suitably, first a mixture of the anti-freeze and water is made which contains a sufficient amount of the anti-freeze to be pourable at the indicated temperatures. This mixture can then be used in the further process to make the emulsions. Although use can be made of most antifreeze agents, such as salts and organic compounds, it is preferred to use organic compounds selected from methanol, ethanol, propanol, isopropanol, glycol, propanediol, and glycerol, since it is known that such compounds will have hardly any effect on polymerization processes in which peroxide emulsions are used. Most preferably, methanol is used as anti-freeze, as the COD value of the aqueous phase is relatively low (vide supra) and, furthermore, because agents such as ethylene glycol, propanol or propane are more likely to end up in the polymer that is formed when aqueous emulsions are used as a source of free radicals in a polymerization process, resulting in less desirable organoleptic properties of the polymer. Also combinations of two or more anti-freeze agents can be used in the emulsions according to the invention. If, for example, ethylene glycol is added in a relatively low amount to a mixture of water and methanol, the flammability will be positively influenced, as the total mixture will be less flammable at the same temperature. It is noted that if the COD value of the aqueous phase should be too high due to the presence of the methanol, then some inorganic salts can be substituted for the organic compound. The amount of anti-freeze is preferably chosen such that the aqueous phase does not freeze at a temperature of −10° C., preferably the emulsion does not freeze at a temperature of −15° C., more preferably the emulsion does not freeze at a temperature of −20° C.

The compositions according to the invention contain a sufficient amount of the surfactants and/or anti-freeze agents for the desired stable and safe aqueous peroxide emulsions to result.

The emulsions according to the invention may, if so desired, comprise one or more thickeners in a concentration up to 2% w/w in order to control the viscosity of the composition. If used, the thickener preferably makes up less than 1% w/w of the emulsion. Non-limiting examples of thickeners useful in the formulation are xanthan gum, Arabic gum, and alginates. However, thickeners are preferably omitted from the aqueous emulsions.

In addition to the above-mentioned compounds, the compositions according to the invention can also comprise other "standard" additives, including pH-adjusting agents such as calcium oxide or phosphate buffers, sequestering agents, and, if desired, biocides, e.g. fungicides. The concentration of these additives will depend on the desired effect and the other ingredients in the emulsion. Given the information presented here, the skilled man will have no problem selecting appropriate concentrations of the individual ingredients in the emulsions of choice, as they will adversely affect the COD value of the aqueous phase.

What is meant by storage stable emulsions is that the products do not separate at the storage temperature and have a volume average peroxydicarbonate droplet size (d50) and a 99 percentile of the droplet size distribution (d99) which do not change by more than 5 μm during twelve weeks of storage. Preferably, the change in d50 is less than 3 μm, more preferably less than 2 μm and most preferably less than 1 μm, since changes in droplet size will influence the viscosity and further storage stability of the emulsion, while also the polymerization process can be adversely influenced when larger peroxide droplets are introduced, e.g., by an increased number of fish-eyes. It is also for this reason that the d50 of the droplet size distribution should be below 10 μm, while a d50 of less than 5 μm, particularly less than 4 μm, is preferred. The droplet size is determined by means of a light scattering technique, using a Malvern® Easy Sizer.

As mentioned above, it is important that the concentrated peroxide emulsions according to the invention have a viscosity that allows easy handling and use. In practice, this means that the product should have a viscosity of less than 1,500 mPa·s, when measured at the recommended storage temperature using an Erichsen viscometer, model 332 (0–1,500 mPa·s). Preferably, the Erichsen viscosity is less than 500 mPa·s. Alternatively, suitable emulsions were found to have a viscosity below 5,000 mPa·s when measured at the same temperature, using a Brookfield LVT with spindle sp3 at 12 rpm. Preferably, the emulsions will have a Brookfield viscosity of less than 3,000 mPa·s.

As is well-known, peroxides are thermally labile organic compounds. Because the decomposition of peroxide is exothermic, it is hazardous when the heat of decomposition cannot be dissipated, e.g., by heat loss to the surrounding area. When heat build-up occurs, the decomposition reaction eventually becomes uncontrollable and potentially dangerous. To avoid such undesired situations, the peroxide is typically formulated with one or more phlegmatizing agents, such as inert organic materials, including water. Aqueous peroxide emulsions are generally considered safe products, because the peroxide is dispersed in the water phase, which is well-suited to the removal of the heat of decomposing peroxide molecules, e.g., by convection and/or evaporation. However, it was observed that many peroxide emulsions according to prior art formulations suffer from the drawback that they show phase separation upon heating, particularly at temperatures where water evaporation becomes noticeable. If so, the peroxide separates out and forms a highly concentrated peroxide phase the heat of decomposition of which is not dissipated. As a result, such aqueous peroxide emulsions can be as hazardous as the neat peroxide. One of the objects of the emulsions according to the invention therefore was to develop formulations that do not form a significant amount of a hazardous phase upon heating.

An emulsion in accordance with the invention is considered to be safe if less than 10% by volume of one or more other phases is formed or, if more than 10% by volume of phase separation were to occur, none of the phases has a peroxide content such that the active oxygen content is greater than 1% w/w. In a discriminating test for "safe" behaviour a sample of the emulsion is kept at a temperature which is 35° C. above the well-known self-accelerating decomposition temperature (SADT) of the peroxide phase present in the emulsion for 8 hours.

The emulsions of the invention can be produced in a conventional manner. Typically, the compounds of the emulsion are mixed and/or homogenized using well-known equipment, such as colloid mills, perl mills, pressure homogenizers, fluidizers, ultrasonic homogenizers, etc. Because many of the peroxydicarbonates are not stable at higher temperatures, the mixing and/or homogenizing should be done below a temperature of 15° C., preferably well below the SADT.

The emulsions of the invention are preferably used in suspension or emulsion polymerization processes. However, they can also be used in other processes, such as polymer modification processes, cross-linking reactions, mass polymerization processes, and curing processes of, for example, unsaturated polyester resins. In these processes a variety of monomers and/or polymers can be reacted, including, for example, acrylates, vinyl esters, vinyl halides, vinyl ethers, vinyl aromatic compounds, such as styrene, lower alkenes, polybutadiene, methacrylate-butadiene-styrene copolymers, and the like. The emulsions therefore can be used, for example, in the mass polymerization of vinyl chloride monomer (VCM). However, the emulsions are more preferably used in suspension or emulsion polymerization processes wherein at least VCM, styrene or a (meth)acrylate is reacted. Most preferred is the use of the emulsions in the suspension polymerization process of predominantly VCM. The emulsions are only usable in these processes when they do not influence the properties of the resulting polymer, or do so only to a very limited extent. In the preferred VCM polymerization process, this means that hardly any fouling is observed and the PVC particle size, porosity, fish-eye number, and electrical properties are hardly affected.

It is noted that all weight percentages as used herein are based on the weight of the total aqueous emulsion.

As will be understood, the COD value is as small as possible, although it can vary over a wide range depending on the ingredients and the amounts in which they are used. Typically, the total COD of the aqueous phase is below 50 mg oxygen per 100 mg emulsion, preferably below 40 mg oxygen per 100 mg emulsion, more preferably below 30 mg oxygen per 100 mg emulsion, even more preferably below 25 mg oxygen per 100 mg emulsion, and most preferably below 20 mg oxygen per 100 mg emulsion. More preferably, the COD value of the aqueous phase in relation to the amount of peroxide in the organic phase is below 2 mg oxygen per 100 mg emulsion per g peroxide, more preferably below 1.5 mg oxygen per 100 mg emulsion per g peroxide, even more preferably below 1.0 mg oxygen per 100 mg emulsion per g peroxide, and most preferably below 0.5 mg oxygen per 100 mg emulsion per g peroxide.

The peroxide emulsions according to the invention and their uses are further illustrated in the following examples.

EXAMPLES

In the examples, the following products and abbreviations were used:
EHP=di(2-ethylhexyl) peroxydicarbonate (TRIGONOX® EHP ex Akzo Nobel)
PVA65=62-68% saponified PVAC
ESA=ethoxylated stearyl alcohol (HLB=18.5)

The aqueous peroxydicarbonate emulsions as described in the following examples comprise EHP, PVA65, optionally ESA, water, and methanol. The amounts of each compound are given in the table.

Comparative Examples A and B

Comparative Examples A and B have an EHP concentration of 50% w/w, with the weight percentage of PVA65 being reduced.

TABLE 1

|  | Example | |
| --- | --- | --- |
|  | A (reference) | B |
| EHP (as pure) (% w/w) | 50 | 50 |
| PVA65 (% w/w) | 3.0 | 1.5 |
| Balance water/methanol (% w/w/% w/w) | 71/29 | 71/29 |
| d99 1 day [micron] | 2.5 | 3.3 |
| d99 4 wks [micron] | 2.8 | 7.2 |
| d50 1 day [micron] | 1.8 | 2.4 |
| d50 4 wks [micron] | 2.0 | 3.2 |
| Separation during storage (4 wks) | none | Very slight |
| Separation safety test | OK | FAIL |
| Erichson [mPa · s] (0° C., 4 Weeks) | 220-205 | 120-90 |
| Brookfield [mPa · s] (0 C., 4 weeks) | 160-190 | 110 |
| Brookfield [mPa · s] (−10° C., 4 weeks) | 2080 | 2304 |

From Comparative Examples A and B in Table 1, it is clear that the average droplet size (d50) grows when less PVA65 is used, as does the 99 percentile droplet size distribution (d99). Also, at lower PVA concentrations an unsafe emulsion results, as follows from the separation safety test as described above. Also more concentrated peroxide emulsions wherein water was replaced by peroxide were found to be unsafe and suffer from viscosity problems.

Examples 1-3

In Example 1 the amount of EHP is increased to 55% w/w, while for the emulsions of Examples 2 and 3, the EHP concentration is increased to about 62 and 61% w/w, respectively. Examples 1-3 further comprise PVA65, ESA, water, and methanol.

TABLE 4

|  | Example | | |
| --- | --- | --- | --- |
|  | 1 | 2 | 3 |
| EHP (as pure) (% w/w) | 55 | ca 62 | ca 61 |
| PVA65(% w/w) | 0.8 | 0.6 | 0.6 |

TABLE 4-continued

|   | Example | | |
|---|---|---|---|
|   | 1 | 2 | 3 |
| ESA (% w/w) | 0.3 | 0.3 | 0.3 |
| Balance water/methanol (% w/w/% w/w) | 69/31 | 69/31 | 69/31 |
| Storage temperature is −15° C. | | | |
| d99, 1 day [micron] | 2.8 | 2.5 | 2.5 |
| d99, 2 weeks [micron] | no data | no data | 2.5 |
| d99, 4 weeks [micron] | 3.8 | 2.9 | no data |
| d99, 8 weeks [micron] | 3.3 | 2.5 | no data |
| d99, 12 weeks [micron] | 3.4 | 2.9 | no data |
| d50, 1 day [micron] | 2.1 | 1.8 | 2.0 |
| d50, 2 weeks [micron] | no data | no data | 2.0 |
| d50, 4 weeks [micron] | 2.5 | 2.0 | no data |
| d50, 8 weeks [micron] | 2.4 | 2.3 | no data |
| d50, 12 weeks [micron] | 2.6 | 2.2 | no data |
| Separation bottom (8 weeks) | None | None | no data |
| Separation top (8 weeks) | None | None | no data |
| Separation top (12 weeks) | 1 mm | no data | no data |
| Separation safety test | OK | OK | no data |
| Erichson [mPa · s] | | | |
| (−10° C., 2 weeks) | no data | no data | 370 |
| (−10° C., 4 weeks) | 300 | 475 | 390 |
| (−10° C., 8 weeks) | 300 | 470 | no data |
| (−10° C., 12 weeks) | no data | 470 | no data |
| (−6° C., 12 weeks) | 255 | no data | no data |
| Brookfield [mPa · s] | | | |
| (−14° C., 2 wks) | no data | no data | 680 |
| (−14° C., 4 wks) | 720 | 2020 | 1010 |
| (−14° C., 8 wks) | 1050 | 2220 | no data |
| (−14° C., 12 wks) | no data | 2590 | no data |
| (−10° C., 12 wks) | 910 | no data | no data |

All examples have low d50 and d99 values compared to the low PVA-containing Example B. These values have not changed significantly after 12 weeks of storage. It follows that a small amount of ESA and a small amount of PVA can be added to make a highly concentrated peroxydicarbonate emulsion with a small average droplet size and a narrow droplet size distribution with a good storage stability and safety. It must further be noted that, despite the high EHP concentration, the viscosity as represented by the Erichson and Brookfield viscosities is relatively low. The low amounts of ESA and PVA ensure that an aqueous phase with a low COD value is obtained, especially a low COD value per gram of peroxide in the formulation. Also the use of methanol ensures that the COD value is low. It shows furthermore that, when compared to conventional peroxide emulsions, the present emulsions surprisingly can be made with a lower COD per 100 g of peroxide.

When evaluated in a conventional suspension polymerization process of vinyl chloride monomer, it was surprisingly found that at equal peroxide loading and equal polymerization conditions, the polymer of the experiments wherein emulsions according to the invention were used showed a significantly reduced number coarse PVC particles and significantly less fish-eyes, the term conventionally used in the industry for defects observed when preparing foils of the polymer. The reduction was seen not only in comparison with experiments in which conventional solutions or pure peroxides were used, but, remarkably, also when compared with experiments wherein conventional peroxide emulsions were used. Illustrative of the effect is the comparison of the analysis of the polymer resulting from a standard suspension polymerization of vinyl chloride using a 10 liter reactor wherein 2.87 kg of vinyl monomer was polymerized using the peroxide emulsions of Example 3 and Comparative Example A.

| Peroxide emulsion from: | Example A | Example 3 |
|---|---|---|
| Coarse PVC particles >800 μm (g) | 4 | 2.4 |
| $D_{50}$ of the PVC particles (wet analysis) | 173 μm | 177 μm |
| Bulk density of the dried PVC powder (kg/m$^3$) | 493 | 494 |
| Porosity of the dried PVC powder (%) (conventional DOP absorption) | 25.3 | 25.3 |
| Fish-eyes (dm$^{-2}$) | 10-11 | 4-7 |

The invention claimed is:

1. An aqueous emulsion, comprising an aqueous phase and a peroxide-containing phase, from 52.5 to 75% by weight of one or more peroxides selected from the group of diacyl peroxides and peroxydicarbonates, from 0.01 to 2.5% by weight of a partly saponified polyvinyl acetate having a degree of hydrolysis of at least 45 and at most 80%, a stabilizing amount of one or more non-ionic surfactants having an HLB value of at least 10, and one or more anti-freeze agents such tat a storage stable and safe formulation results, wherein the aqueous phase has a total chemical oxygen demand (COD) of less than 20 mg of oxygen per 100 mg of the emulsion, and the percentages by weight are based on the weight of the aqueous emulsion.

2. An aqueous emulsion according to claim 1 wherein the non-ionic surfactant is an ethoxylated fatty alcohol having an HLB value of at least 15.

3. An aqueous emulsion according to claim 2 wherein the ethoxylated fatty alcohol is present in an amount from 0.001 to 5% by weight.

4. An aqueous emulsion according to claim 1 wherein the anti-freeze agent is a compound selected from the group consisting of methanol, ethanol, isopropanol, glycol, propanediol, glycerol, and combinations thereof, and is used in a quantity such that the emulsion does not freeze at a temperature of −10° C.

5. An aqueous emulsion according to claim 1 wherein the volume average droplet size of the peroxide-containing phase is less than 4 μm.

6. An aqueous emulsion according to claim 1 wherein the peroxides comprise one or more peroxydicarbonates.

7. A process wherein an emulsion according to claim 1 is used as a source of free radicals.

8. A process according to claim 7 wherein one or more ethylenically unsaturated monomers is polymerized.

9. A process according to claim 8 wherein vinyl chloride is polymerized, optionally together with other monomers and/or in the presence of a polymer.

10. An aqueous emulsion according to claim 1 wherein the non-ionic surfactant is an ethoxylated fatty alcohol having an HLB value of at least 16.

11. An aqueous emulsion according to claim 1 wherein the non-ionic surfactant is an ethoxylated fatty alcohol having an HLB value of at least 17.

12. An aqueous emulsion according to claim 2 wherein the ethoxylated fatty alcohol is present in a amount from 0.001 to 1% by weight.

13. An aqueous emulsion according to claim 10 wherein the ethoxylated fatty alcohol is present in an amount from 0.001 to 1% by weight.

14. An aqueous emulsion according to claim 11 wherein the ethoxylated fatty alcohol is present in an amount from 0.001 to 1% by weight.

15. An aqueous emulsion according to claim 1 wherein the anti-freeze agent is a compound selected from the group consisting of methanol, ethanol, isopropanol, glycol, propanediol, glycerol, and combinations thereof, and is used in a quantity such that the emulsion does not freeze at a temperature of −15° C.

16. An aqueous emulsion according to claim 1 wherein the anti-freeze agent is a compound selected from the group consisting of methanol, ethanol, isopropanol, glycol, propanediol, glycerol, and combinations thereof, and is used in a quantity such that the emulsion does not freeze at a temperature of −20° C.

* * * * *